(12) United States Patent
Vernica (10) Patent No.: US 11,590,019 B2
(45) Date of Patent: Feb. 28, 2023

(54) URINARY DEVICE FOR MALES

(71) Applicant: Mike Vernica, Whittier, CA (US)

(72) Inventor: Mike Vernica, Whittier, CA (US)

( * ) Notice: Subject to any disclaimer, the term of this patent is extended or adjusted under 35 U.S.C. 154(b) by 12 days.

(21) Appl. No.: 17/497,598

(22) Filed: Oct. 8, 2021

(65) Prior Publication Data

US 2022/0354686 A1 Nov. 10, 2022

Related U.S. Application Data (63) Continuation-in-part of application No. 17/313,498, filed on May 6, 2021, now abandoned.

(51) Int. Cl.
| | |
|---|---|
| *A47K 13/08* | (2006.01) |
| *A61F 5/453* | (2006.01) |
| *E03D 11/18* | (2006.01) |
| *E03D 13/00* | (2006.01) |
| *E03D 11/02* | (2006.01) |

(52) U.S. Cl.
CPC ............. *A61F 5/453* (2013.01); *A47K 13/08* (2013.01); *E03D 11/025* (2013.01); *E03D 11/18* (2013.01); *E03D 13/005* (2013.01)

(58) Field of Classification Search
CPC ........ A47K 11/12; A47K 13/08; A47K 17/00; A61F 5/453; E03D 1/22; E03D 11/025; E03D 11/125; E03D 13/00–007
See application file for complete search history.

(56) References Cited

U.S. PATENT DOCUMENTS

| | | | | |
|---|---|---|---|---|
| 1,549,321 | A | | 10/1985 | Douillard |
| 4,549,321 | A | * | 10/1985 | Douillard ............... E03D 13/00 4/312 |
| 5,134,728 | A | | 8/1992 | Sturm |
| 5,153,947 | A | * | 10/1992 | Markles .................. E03D 13/00 4/342 |
| 5,390,374 | A | | 2/1995 | Hubrig |
| 6,089,807 | A | * | 7/2000 | Larsson ................. A47K 13/26 411/433 |
| 9,605,420 | B1 | * | 3/2017 | Berger ................... E03D 11/025 |
| 10,851,535 | B2 | * | 12/2020 | Gajo ...................... E03D 11/025 |
| 2016/0289945 | A1 | * | 10/2016 | Seneff ..................... A47K 13/08 |
| 2021/0121027 | A1 | | 4/2021 | Stikes, III |

FOREIGN PATENT DOCUMENTS

| | | | | |
|---|---|---|---|---|
| DE | 102010046698 | * | 3/2012 | ........... E03D 11/025 |
| GB | 2467001 | | 7/2010 | |

* cited by examiner

*Primary Examiner* — David P Angwin
*Assistant Examiner* — Nicholas A Ros
(74) *Attorney, Agent, or Firm* — Averill, Green & Kim; Kenneth L. Green; Philip Y Kim (57) ABSTRACT

A urinary device is attachable to a toilet and assists males in directing a flow of urine into the toilet. The device is installed between a toilet seat and tank and pivots to a vertical or near vertical position against the tank when not in use. A telescoping portion extends for tall or short males. The device may be installed on any standard toilet in a few minutes. A bypass may be included to direct urine into a drain avoiding the toilet bowl and the need to flush the toilet. The urinary device reduces or eliminates germs and odors on or around the toilet and is easy to clean using water and a household cleaner.

15 Claims, 8 Drawing Sheets

URINARY DEVICE FOR MALES

CROSS-REFERENCE TO RELATED APPLICATIONS

The present application is a Continuation In Part of U.S. patent application Ser. No. 17/313,498 filed May 6, 2021, which application is incorporated in its entirety herein by reference.

BACKGROUND OF THE INVENTION

The present invention relates to urinary devices and in particular to devices for assisting males have difficulty controlling urination.

Millions of males have prostate related urinary problems and can't control a flow during urination and more then 85% of males over the age of 55 have prostate problems. The prostate problems cause an erratic urine stream from the bladder making it difficult to direct a flow of urine into a toilet while standing.

Many older males often sit to urinate but may have trouble getting back up. Others who drink also have trouble directing a flow of urine into a toilet from a standing position. There is therefore a need for a product to assist older males while urinating.

There is a further need to reduce water use due to water shortages. Residential toilets use much more water than necessary when used for urinating.

BRIEF SUMMARY OF THE INVENTION

The present invention addresses the above and other needs by providing a urinary device attachable to a toilet and assists males in directing a flow of urine into the toilet. The device is installed between a toilet seat and tank and is biased by a spring to a vertical or near vertical position against the tank when not in use. A telescoping portion extends for tall or short males. The device may be installed on any standard toilet in a few minutes. A base is sandwiched between a toilet seat and tank and includes an extension directing the flow of urine into the toilet bowl. A bypass may be included to direct urine into a drain avoiding the toilet bowl and the need to flush the toilet. The urinary device reduces or eliminates germs and odors on or around the toilet and is easy to clean using water and a household cleaner.

In accordance with one aspect of the invention, there is provided a urinary device which adjusts for each user. The urinary device pivots at its base and telescopes.

In accordance with another aspect of the invention, there is provided a urinary device having simple installation. The urinary device includes a fixed base sandwiched between a toilet seat and bowl. The base includes slots or holes receiving standard studs fixed to the seat and retaining the seat on the bowl.

In accordance with yet another aspect of the invention, there is provided an easy to clean urinary device. The urinary device is biased by a spring to a vertical position to drain and is easily cleaned by running a flow of water or a water cleaner mixture through the urinary device.

In accordance with still another aspect of the invention, there is provided a water saving urinary device. The urinary device includes a bypass to direct the urine flow to release urine into a flow in a toilet pedestal bypassing the toilet bowl and eliminating a need to flush the toilet after urinating.

BRIEF DESCRIPTION OF THE SEVERAL VIEWS OF THE DRAWING

The above and other aspects, features and advantages of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing one or more preferred embodiments of the invention. The scope of the invention should be determined with reference to the claims.

Where the terms "about" or "generally" are associated with an element of the invention, it is intended to describe a feature's appearance to the human eye or human perception, and not a precise measurement, or typically within 10 percent of a stated value.

Figure 1A:
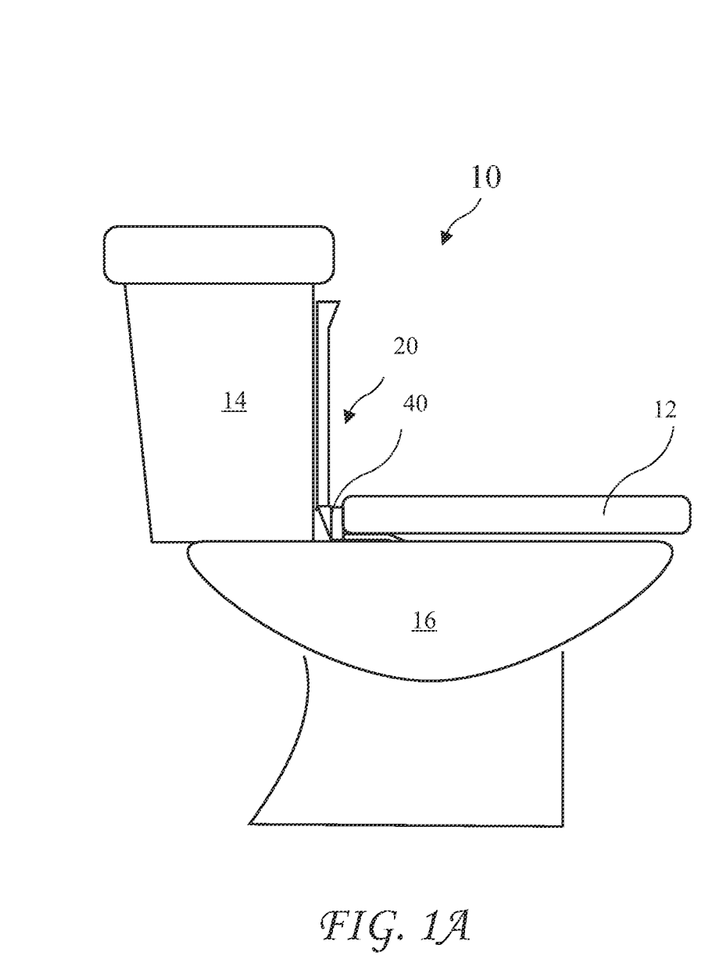
FIG. 1A shows a urinary device according to the present invention in a vertical position against a toilet tank.
Figure 1B:
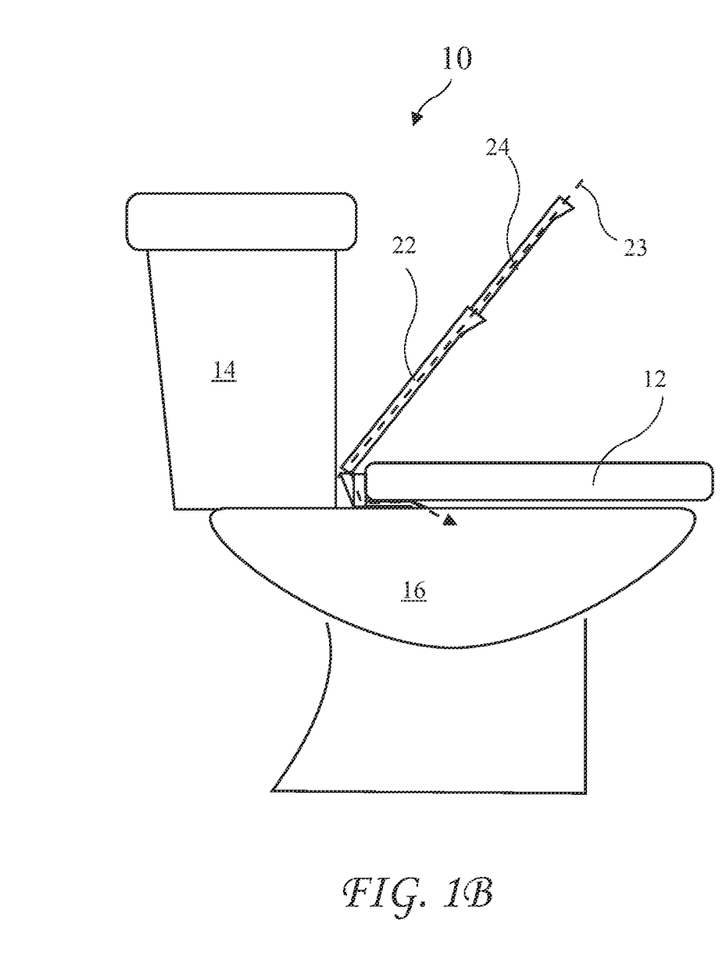
FIG. 1B shows the urinary device according to the present invention pivoted and extended for use.

A urinary device 20 according to the present invention is shown attached to a toilet 10 in a vertical position and pivoted against a tank 14 in FIG. 1A and the urinary device 20 is shown pivoted away from the tank 14 and extended for use in FIG. 1B. The urinary device 20 includes a body portion 22 hingedly connected to a base 40 which is sandwiched between a seat 12 and a bowl 16. An extension 24 extends from a body portion 22 to receive a urine flow 23 released into the bowl 16. In the following description and claims, a direction toward a toilet tank 14 is referred to as rearward, and a direction away from the toilet tank 14 and over the toilet bowl 16 is referred to as forward.

Figure 2A:
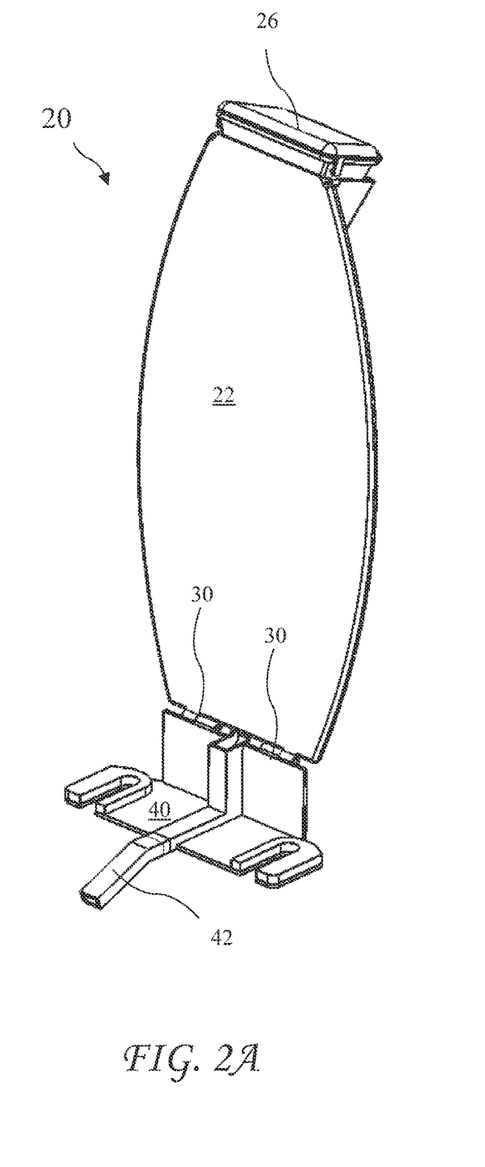
FIG. 2A is a front and side view of the urinary device according to the present invention.
Figure 2B:
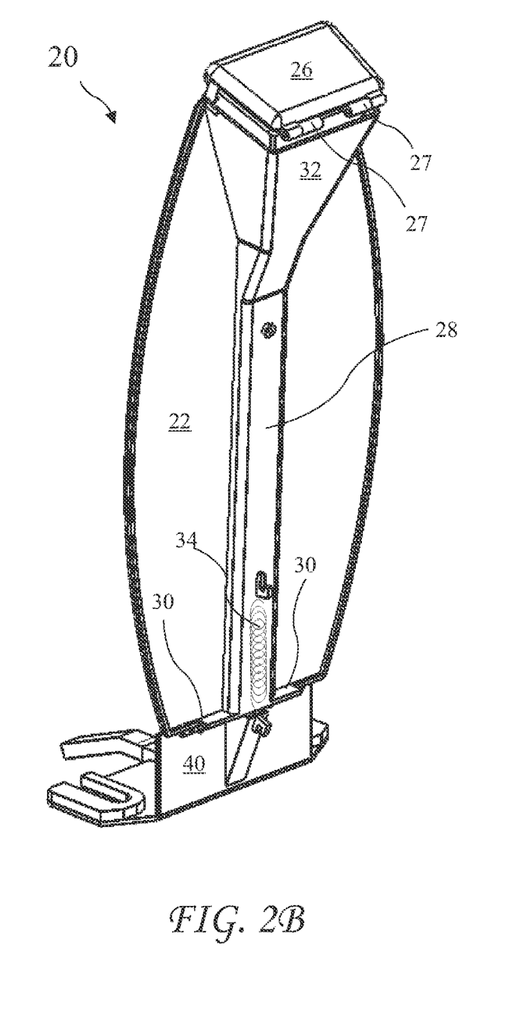
FIG. 2B is a rear and side view of the urinary device according to the present invention.

A front and side view of the urinary device 20 is shown in FIG. 2A and a rear and side view of the urinary device 20 is shown in FIG. 2B. The body portion 22 is connected to the base 40 by hinges 30. A lid 26 is attached to the extension 23 by hinges 27 to open and close a funnel 32a of the extension 23 for use. A spring 34 connected between a first hook 32a (see FIG. 3C) of the body portion 22 and a second hook 36b (see FIG. 5B) of the base 40 is in tension to bias the body portion 22 against the tank 14 when not is use. A tunnel 28 below a funnel portion 32 in the body portion 22 is provided for the extension 24.

Figures 3, 3A, 3B, 3C, 3D, 3E:
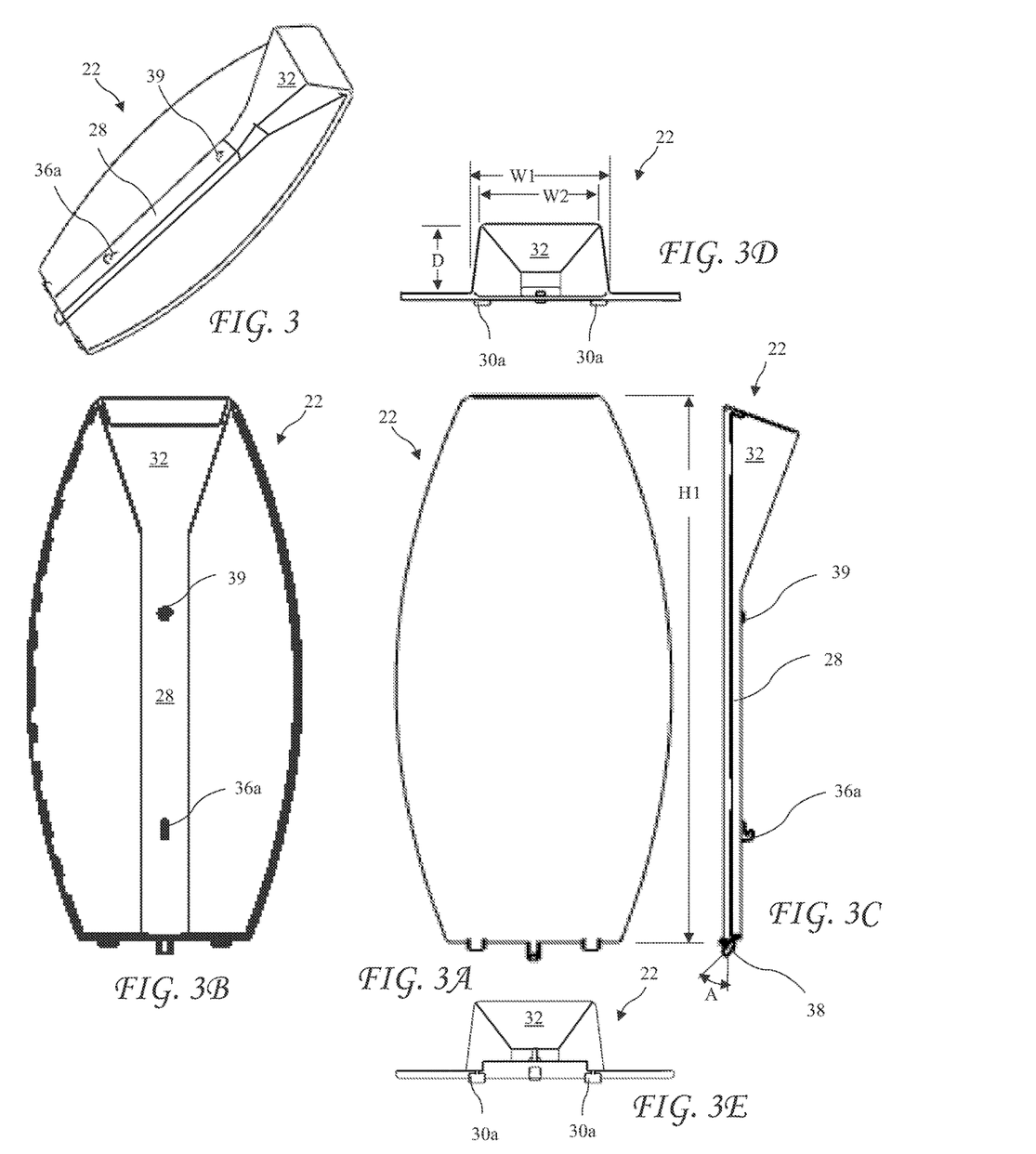
FIG. 3 shows a perspective view of a body portion of the urinary device according to the present invention.
FIG. 3A shows a front view of a body portion of the urinary device according to the present invention
FIG. 3B shows a rear view of the body portion of the urinary device according to the present invention.
FIG. 3C shows a side view of the body portion of the urinary device according to the present invention.
FIG. 3D shows a top view of the body portion of the urinary device according to the present invention.
FIG. 3E shows a bottom view of the body portion of the urinary device according to the present invention.

A perspective view of the body portion 22 is shown in FIG. 3, a front view of the body portion 22 is shown in FIG. 3A, a rear view of the body portion 22 is shown in FIG. 3B, a side view of the body portion 22 is shown in FIG. 3C, a top view of the body portion 22 is shown in FIG. 3D, and a bottom view of the body portion 22 is shown in FIG. 3E. The body portion 22 includes an extension retainer 39 reaching into the tunnel 28 and engaging a slot 25 in the extension tube 29 to limit withdrawal of the extension 24 from the body portion 22. The extension retainer 39 may be a screw through the body portion 22 or molded into the body portion 22, and a screw may be removed to remove the extension 24 for cleaning or removing an object accidentally dropped into the extension 24. An elbow 38 at the bottom of the tunnel 28 aligns with a mouth 50 in the base 40.

The elbow 38 is arced an angle A of preferably between 30 and 60 degrees, and more preferably about 45 degrees, and most preferably 45 degrees. The body portion 20 has a height H1 of preferably between 13 and 18 inches, and more preferably about 16 inches, and most preferably is 16 inches. The funnel portion 32 has widths W1 and W2. The width W1 preferably between 3.5 and 4.5 inches, and more preferably about 4 inches, and most preferably is 4 inches. The width W2 preferably between 3 and 4 inches, and more preferably about 3.5 inches, and most preferably is 3.5 inches. The width W2 may also be described as about 0.5 inches narrower than the width W1.

Figure 4:
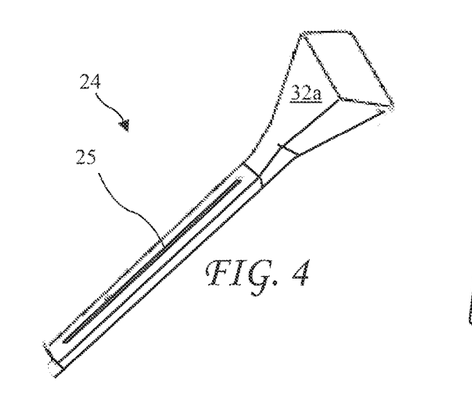
FIG. 4 shows a perspective view of an extension portion of the urinary device according to the present invention.
Figures 4A, 4C, 4E:
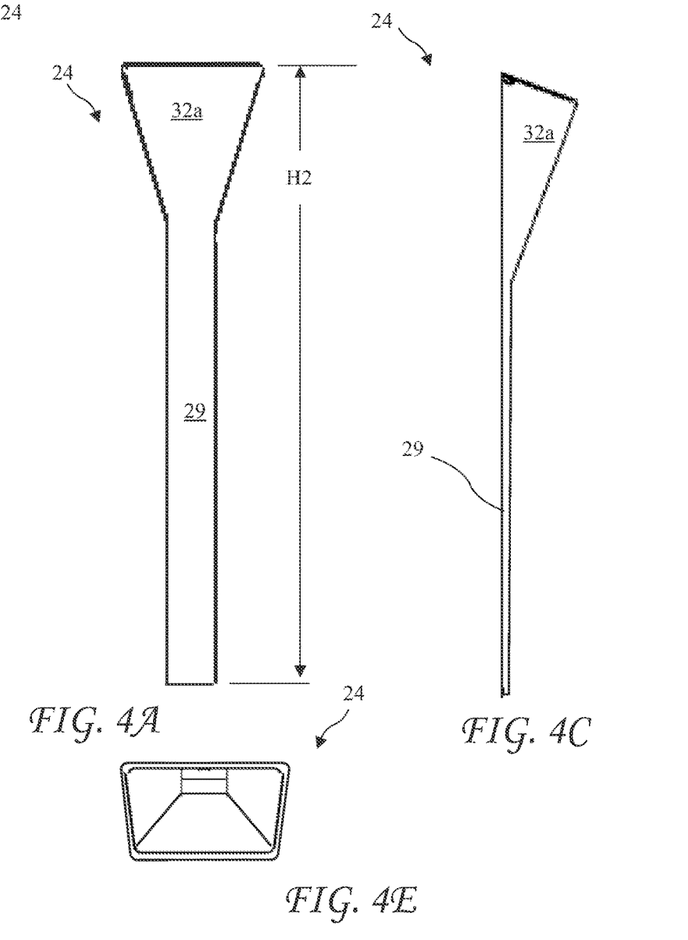
FIG. 4A shows a front view of an extension portion of the urinary device according to the present invention
FIG. 4C shows a side view of the extension portion of the urinary device according to the present invention.
FIG. 4E shows a bottom view of the extension portion of the urinary device according to the present invention.
Figure 4B:
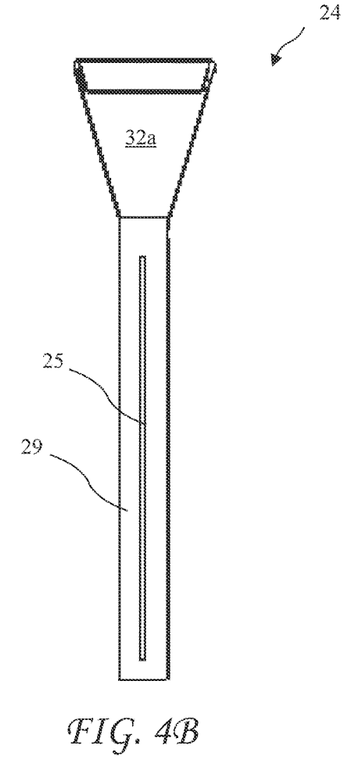
FIG. 4B shows a rear view of the extension portion of the urinary device according to the present invention.
Figure 4D:
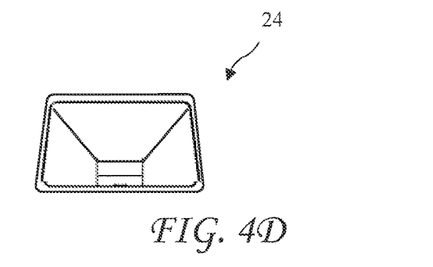
FIG. 4D shows a top view of the extension portion of the urinary device according to the present invention.

A perspective view of the extension portion 24 is shown in FIG. 4, a front view of the extension 24 is shown in FIG. 4A, a rear view of the extension 24 is shown in FIG. 4B, a side view of the extension 24 is shown in FIG. 4C, a top view of the extension 24 is shown in FIG. 4D, and a bottom view of the extension 24 is shown in FIG. 4E. The extension 24 includes a funnel 32a at the top of the extension 24, and the slot 25 on the rear of the tube 29. The extension 24 has a height H2. The height H2 is preferably between 12 and 17 inches, and more preferably about 15 inches, and most preferably is 15 inches. Generally, the height H2 is preferably less than the height H1 and more preferably about one inch less than the height H1.

Figure 5:
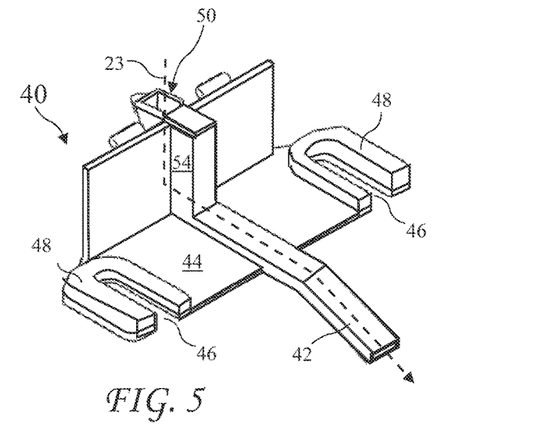
FIG. 5 shows a perspective view of a base portion of the urinary device according to the present invention.
Figure 5A:
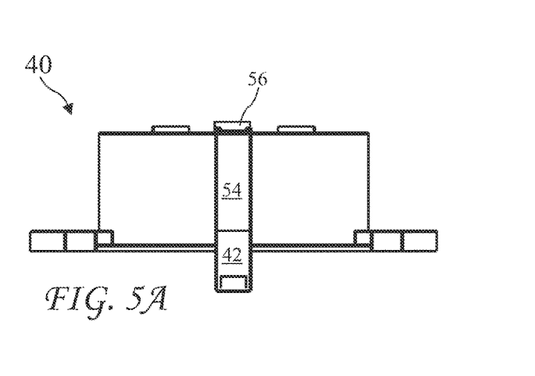
FIG. 5A shows a front view of a base portion of the urinary device according to the present invention
Figure 5B:
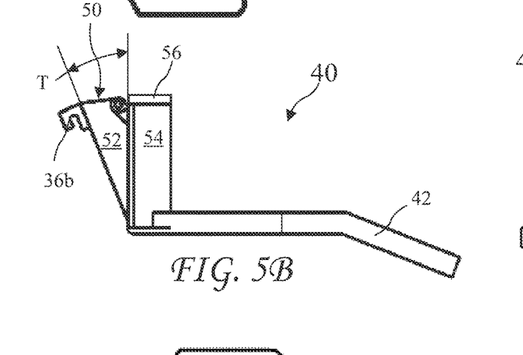
FIG. 5B shows a side view of the base portion of the urinary device according to the present invention.
Figure 5C:
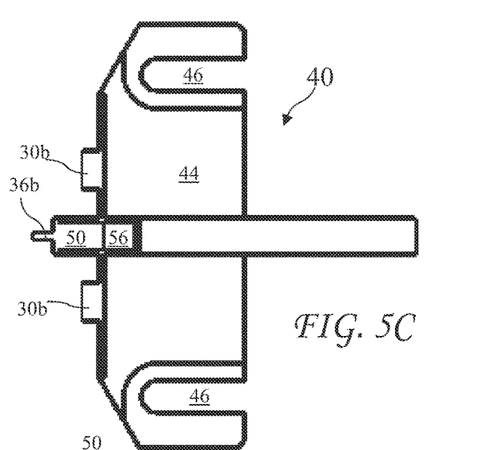
FIG. 5C shows a top view of the base portion of the urinary device according to the present invention.
Figure 5D:
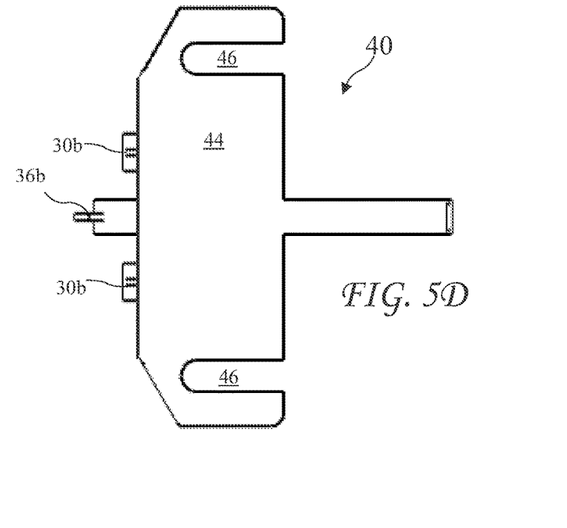
FIG. 5D shows a bottom view of the base portion of the urinary device according to the present invention.

A perspective view of a base 40 of the urinary device 20 is shown in FIG. 5, a front view of a base 40 of the urinary device 20 is shown in FIG. 5A, a side view of a base 40 of the urinary device 20 is shown in FIG. 5B, a top view of a base 40 of the urinary device 20 is shown in FIG. 5C, and a bottom view of a base 40 of the urinary device 20 is shown in FIG. 5D. The base 40 includes a horizontal platform 44 sandwiched between the seat 12 and bowl 16. The horizontal platform 44 has two passages 46 spaced apart for studs attaching the seat 12 to the bowl 16. The passages 46 may be slots or holes, the holes requiring removing the seat 12 to attach the urinary device 20 to the toilet 10. Spacers 48 reside on a top surface of the horizontal platform 44 to lift a rear of a toilet seat 12 to provide space for the spout 42 to pass under a toilet seat 12.

The base 40 includes a vertical passage 52 tilted back a tilt T of preferably between 15 and 30 degrees and more preferably about 21 degrees and most preferably 21 degrees, and having a mouth 50 aligned with the elbow 38 to receive the flow 23 from the body portion 22. A relief 54 includes a cover 56. The relief 54 provides space for the elbow 38 (see FIG. 3C) when the urinary device 20 is returned to a near vertical position. The flow 23 passes from the vertical passage 41 into a spout 42 extending forward over the bowl 16 to release the flow 23 into the bowl 23. The hook 36b is on the rear of the vertical passage 52.

Figure 6A:
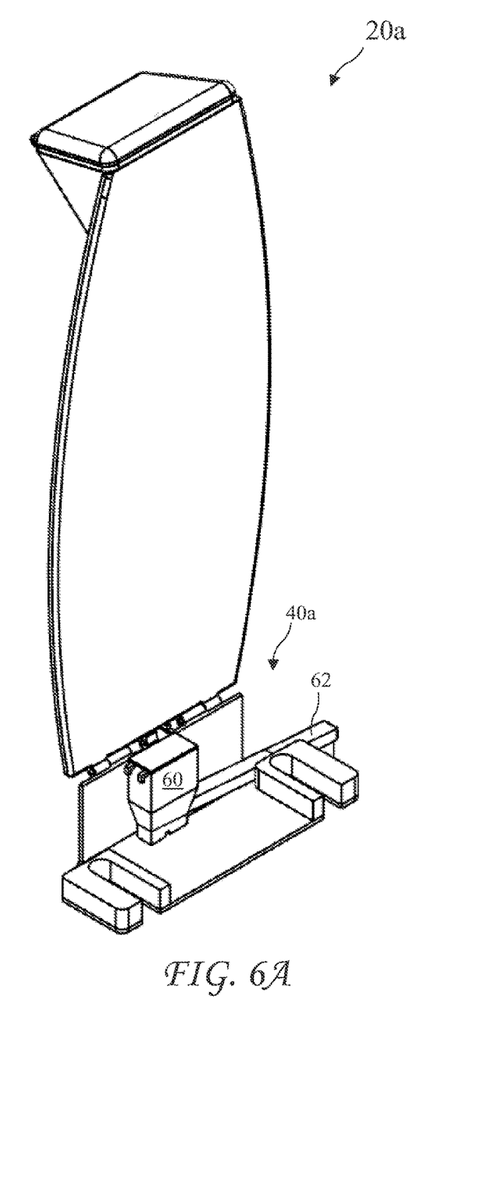
FIG. 6A shows a front and right side view of a water saving urinating device according to the present invention.
Figure 6B:
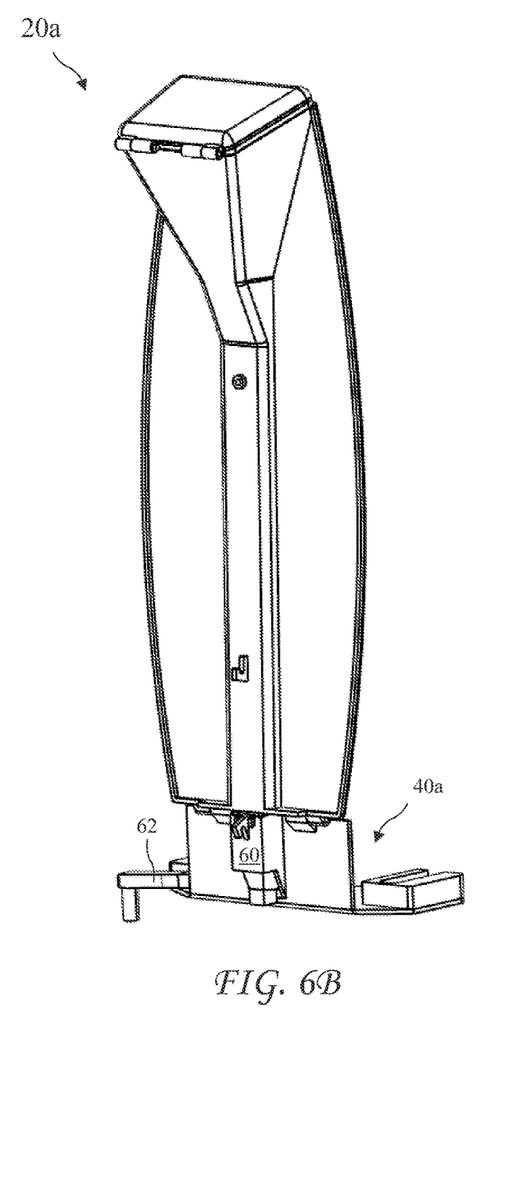
FIG. 6B shows a rear and left side view of the water saving urinating device according to the present invention.

A front and right side view of a water saving urinating device 20a is shown in FIG. 6A and a rear and left side view of the water saving urinating device 20a is shown in FIG. 6B. The water saving urinating device 20a includes a base 40a and a drain 60 attached to the base 40a and having an adjustable spout 62 which may be directed forward as in the instance of the urinating device 20a to drain into the toilet bowl 16, or to the left side.

Figures 7A, 7B, 8A, 8B, 8C:
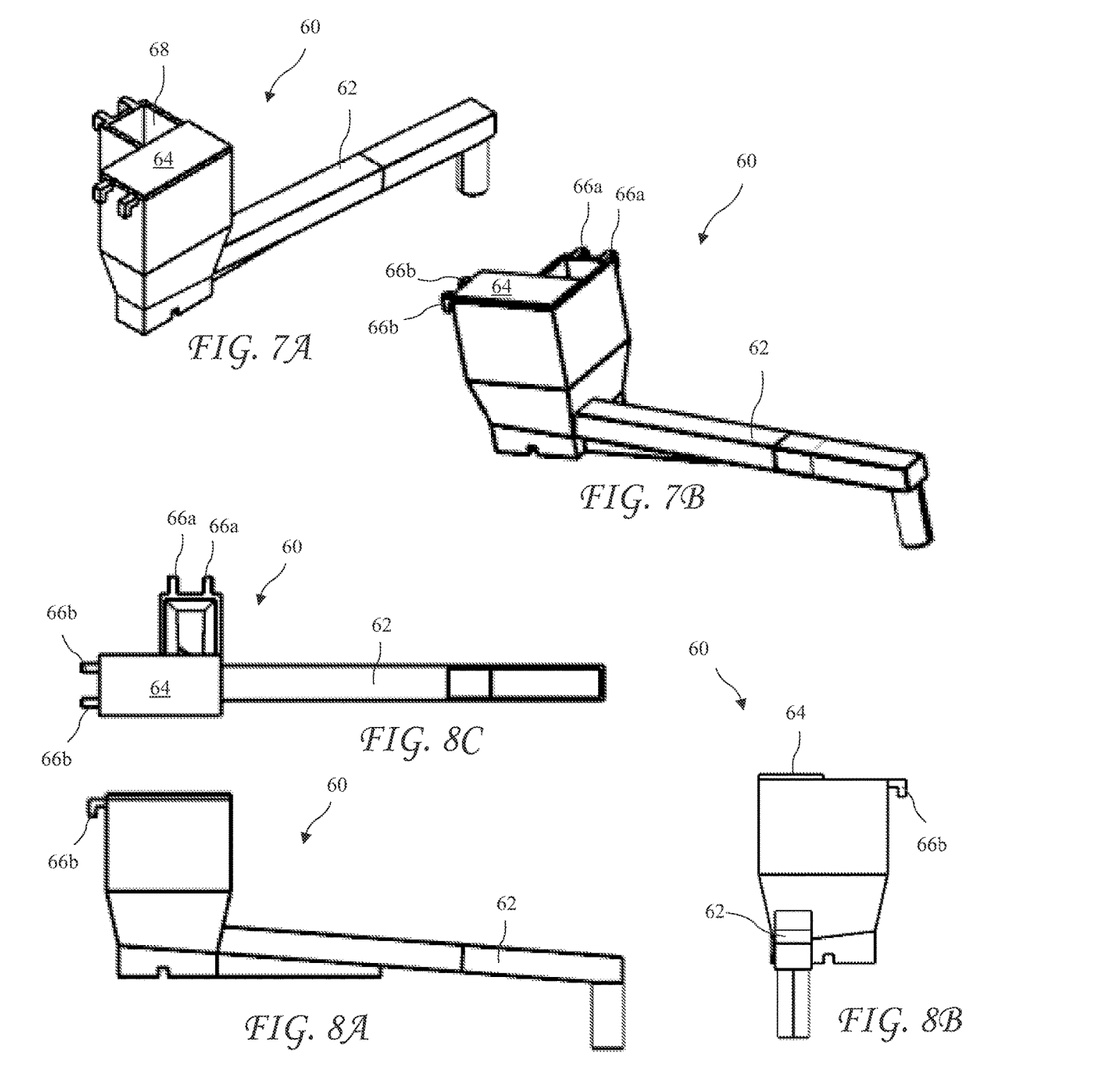
FIG. 7A shows a front and right side view of a drain of the water saving urinating device according to the present invention.
FIG. 7B shows a front and left side view of the drain of the water saving urinating device according to the present invention.
FIG. 8A shows a front view of the drain of the water saving urinating device according to the present invention.
FIG. 8B shows a left side view of the drain of the water saving urinating device according to the present invention.
FIG. 8C shows a top view of the drain of the water saving urinating device according to the present invention.

A front and right side view of the drain 60 is shown in FIG. 7A, a front and left side view of the drain 60 is shown in FIG. 7B, a front view of the drain 60 is shown in FIG. 8A, a left side view of the drain 60 is shown in FIG. 8B, and a top view of the drain 60 is shown in FIG. 8C. The drain 60 includes the spout 62 in fluid communication with the tunnel 28 (see FIG. 2B) to release urine from the water saving urinating device 20a. The drain 60 may be attached to the base 40a (see FIG. 6A) as shown to position the spout 60 to the left, or forward similar to the spout 42 (see FIG. 2A). The drain 60 includes hooks 66a and 66b. The hooks 66a may engage the base 40a to retain the drain 60 with the spout 62 reaching to the left as shown, or the drain 60 may be pivoted 90 degrees and the hooks 66b engage the base 40a to retain the drain 60 with the spout 62 reaching forward. A cap 64 partially closes an entry (or vertical passage) 68 into the drain 60. The cap 64 may be detached, pivoted 90 degrees, and reattached when the drain 60 is pivoted, to prevent material from unintentionally entering the drain 60.

Figure 9:
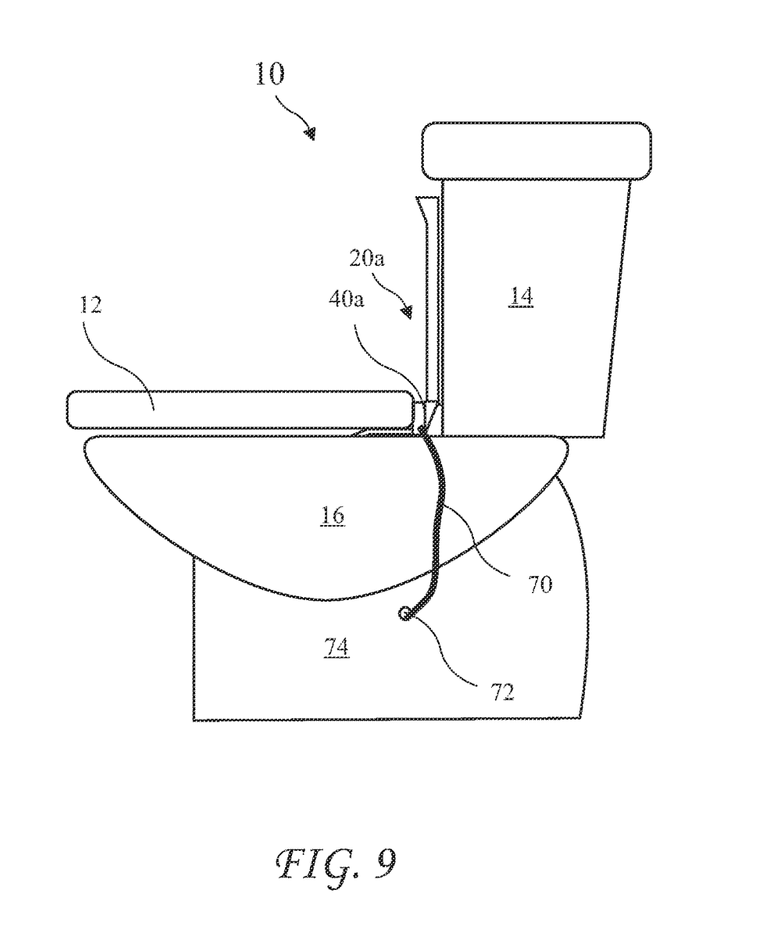
FIG. 9 shows the water saving urinating device according to the present invention attached to a toilet.

The water saving urinating device 20a is shown attached to the toilet 10 in FIG. 9. A hose 70 is attached to the spout 62 and releases urine into a flow in a toilet pedestal 74. Such release of urine eliminates a need to flush the toilet after urinating. The water saving urinating device 20a may further include a valve, not shown, connected to a water supply, and releasing a small flow of water into the funnel 32 or 32a when the funnel is returned to a vertical position after use, to rinse the water saving urinating device 20a.

Figure 10:
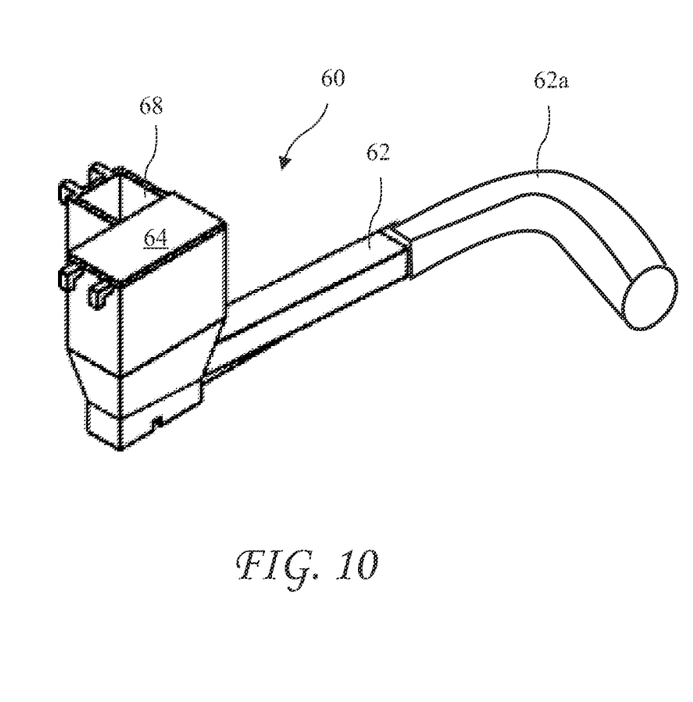
FIG. 10 shows an extension attached to a spout according to the present invention.

An extension 62a attached to the spout 62 is shown in FIG. 10. The extension 62a may be a hose, a plastic tube, or any suitable extension, and may be attached to the spout 62 or directly attached to the drain 60.

The urinary device is preferably made from a plastic material, for example, a plastic grade H 110 MA Dtis material.

While the invention herein disclosed has been described by means of specific embodiments and applications thereof, numerous modifications and variations could be made thereto by those skilled in the art without departing from the scope of the invention set forth in the claims.

I claim:

1. A urinary device comprising:
   a base comprising:
      a horizontal platform configured to reside between a toilet seat and toilet bowl, the horizontal platform including attachment passages spaced apart by a toilet seat stud spacing;
      a vertical passage residing behind the attachment passages and reaches upward from the horizontal platform;
      a movable drain in fluid communication with the vertical passage; and
      a spout in fluid communication with the drain and reaching horizontally from the drain;
   a body reaching up from the base and movably attached to the base, the body including a tunnel reaching from a top to a bottom of the body and in fluid communication with the vertical passage;
   wherein the drain is positionable to extend the spout laterally from the vertical passage past the base and past the toilet bowl, or to extend the spout forward over the toilet bowl.

2. The urinary device of claim 1, further including an extension comprising a tube slidable in the tunnel and in fluid communication with the tunnel,
   wherein the extension includes a slot and the body includes an extension retainer engaging the slot to retain the extension in the body.

3. The urinary device of claim 1, further including an extension comprising:
   a tube slidable in the tunnel and in fluid communication with the tunnel;
   an extension funnel top above the tube and in fluid communication with the tube; and
   a lid configured to close the extension funnel top.

4. The urinary device of claim 1, wherein the vertical passage is tilted back a tilt between 15 and 30 degrees.

5. The urinary device of claim 1, wherein:
   the body includes an elbow extending down and forward from the bottom of the body and into the vertical passage; and
   the elbow in fluid communication with the vertical passage.

6. The urinary device of claim 5, wherein:
   the base includes a relief residing below the vertical passage and open to the vertical passage; and
   the vertical passage in fluid communication with the relief.

7. The urinary device of claim 6, wherein a cap covers the relief.

8. The urinary device of claim 1, wherein the attachment passages are slots.

9. The urinary device of claim 8, wherein spacers are positionable on top surface of the horizontal platform to lift a rear of a toilet seat to provide space for the spout to pass under a toilet seat.

10. The urinary device of claim 1, wherein the spout extends laterally from the vertical passage past the base and past the toilet bowl.

11. The urinary device of claim 10, wherein:
    the spout is in fluid commination with a hose; and
    the hose is in fluid communication with waste flows in a toilet pedestal of the toilet.

12. The urinary device of claim 1, wherein the body is between 13 and 18 inches high.

13. The urinary device of claim 12, further including an extension comprising a tube slidable in the tunnel and in fluid communication with the tunnel,
    wherein the extension is between 12 and 17 inches high.

14. A uninary device comprising:
    a base comprising:
       a horizontal platform configured to reside between a toilet seat and toilet bowl, the horizontal platform including attachment passages spaced apart by a toilet seat stud spacing;
       a vertical passage residing behind the attachment passages and reaches upward from the horizontal platform; and
       a spout in fluid communication with the vertical passage and reaching horizontally from the vertical passage, the spout comprising an arm configured to reach past the base, or an arm and extension configured to reach past the base, or an extension reaching past the base; and
    a body movable attached to the base, the body including a tunnel reaching from at top to a bottom of the body and in fluid communication with the vertical passage;
    wherein:
    the base includes a lower hook and the body includes an upper hook; and
    a spring in tension connects the upper hook to the lower hook and urges the body rearward.

15. A urinary device comprising:
    a base comprising:
       a horizontal platform configured to reside between a toilet seat and toilet bowl, the horizontal platform including attachment passages spaced apart by a toilet seat stud spacing;
       a vertical passage residing behind the attachment passages and reaching upward and rearward from the horizontal platform at a tilt of 21 degrees;
       a lower hook on the vertical passage extending opposite to the attachment passages; and
       a spout in fluid communication with the vertical passage and reaching from the vertical passage past the attachment passages;

a body hingedly attached to the base and having a body height of 16 inches, the body comprising:
 a body funnel top;
 a tunnel reaching from a bottom to the body funnel top and in fluid communication with the body funnel top and the vertical passage; and
 an upper hook on the tunnel above the lower hook and extending opposite to the attachment passages;
an extension having an extension height shorter than the body height and comprising:
 a tube slidable in the tunnel and in fluid communication with the tunnel; and
 an extension funnel top in fluid communication with the tube; and
a spring in tension between the upper hook and the lower hook.

\* \* \* \* \*